United States Patent [19]
Gordon et al.

[11] Patent Number: 5,928,246
[45] Date of Patent: Jul. 27, 1999

[54] STENT SECURING CATHETER

[75] Inventors: Lucas S. Gordon, Redmond; Hanh To, Bellevue, both of Wash.

[73] Assignee: BSC Northwest Technology Center, Inc., Redmond, Wash.

[21] Appl. No.: 08/950,641

[22] Filed: Oct. 15, 1997

[51] Int. Cl.⁶ .................................................. A61F 11/00
[52] U.S. Cl. ........................................ 606/108; 606/159
[58] Field of Search ................................ 606/108, 194, 606/195; 623/1, 11; 604/53

[56] References Cited

U.S. PATENT DOCUMENTS

| | | | |
|---|---|---|---|
| 2,944,552 | 7/1960 | Cannon | 128/304 |
| 3,421,509 | 1/1969 | Fiore | 128/349 |
| 3,657,744 | 4/1972 | Ersek | 128/334 |
| 3,842,441 | 10/1974 | Kaiser | 128/335 |
| 3,993,078 | 11/1976 | Bergentz et al. | 128/334 |
| 4,130,904 | 12/1978 | Whalen | 138/122 |
| 4,140,126 | 2/1979 | Choudhury | 128/325 |
| 4,313,231 | 2/1982 | Koyamada | 128/334 |
| 4,315,509 | 2/1982 | Smit | 128/303 |
| 4,434,797 | 3/1984 | Silander | 128/343 |
| 4,483,339 | 11/1984 | Gillis | 128/334 |
| 4,512,338 | 4/1985 | Balko et al. | 128/341 |
| 4,562,596 | 1/1986 | Kornberg | 623/1 |
| 4,594,996 | 6/1986 | Ibrahim et al. | 128/1 R |
| 4,732,152 | 3/1988 | Wallsten et al. | 128/343 |
| 4,733,665 | 3/1988 | Palmaz | 128/343 |
| 4,739,762 | 4/1988 | Palmaz | 128/343 |
| 4,744,366 | 5/1988 | Jang | 128/344 |
| 4,776,337 | 10/1988 | Palmaz | 128/343 |
| 4,793,348 | 12/1988 | Palmaz | 128/325 |
| 4,800,882 | 1/1989 | Gianturco | 128/343 |
| 4,850,960 | 7/1989 | Grayzel | 604/53 |
| 4,886,062 | 12/1989 | Wiktor | 128/343 |
| 4,907,336 | 3/1990 | Gianturco | 29/515 |
| 4,913,141 | 4/1990 | Hillstead | 606/108 |
| 4,921,478 | 5/1990 | Solano et al. | 604/53 |
| 4,932,959 | 6/1990 | Horzewski et al. | 606/194 |
| 5,026,377 | 6/1991 | Burton et al. | 606/108 |
| 5,053,013 | 10/1991 | Ensiminger et al. | 604/167 |
| 5,156,596 | 10/1992 | Balbierz et al. | 604/164 |
| 5,275,605 | 1/1994 | Winkler | 606/128 |
| 5,330,482 | 7/1994 | Gibbs et al. | 606/113 |
| 5,334,208 | 8/1994 | Soehendra et al. | 606/108 |
| 5,388,590 | 2/1995 | Horrigan et al. | 128/772 |
| 5,409,495 | 4/1995 | Osborn | 606/108 |
| 5,411,507 | 5/1995 | Heckele | 606/108 |
| 5,474,563 | 12/1995 | Myler et al. | 606/108 |
| 5,520,697 | 5/1996 | Lindenberg et al. | 606/108 |
| 5,628,754 | 5/1997 | Shevlin et al. | 606/108 |
| 5,634,937 | 6/1997 | Mollenauer et al. | 606/213 |
| 5,817,100 | 10/1998 | Igaki | 606/108 |

FOREIGN PATENT DOCUMENTS

| | | |
|---|---|---|
| 0 274 846 | 7/1988 | European Pat. Off. |
| 2 104 673 | 5/1972 | Germany |

*Primary Examiner*—Michael Buiz
*Assistant Examiner*—Vy Q. Bui
*Attorney, Agent, or Firm*—Crompton, Seager & Tufte

[57] ABSTRACT

A stent securing catheter including a tubular body having a longitudinal axis and defining a stent receiving lumen. The tubular body having a proximal end and a distal end wherein the distal end defines an opening into the receiving lumen. The opening into the receiving lumen is disposed at a generally acute angle to the longitudinal axis of the tubular body.

6 Claims, 1 Drawing Sheet

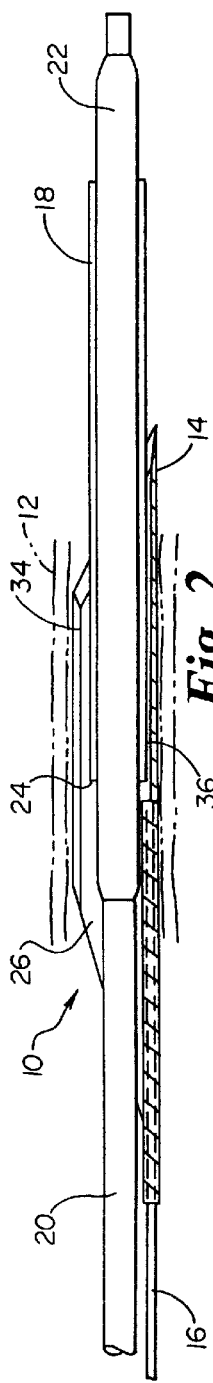
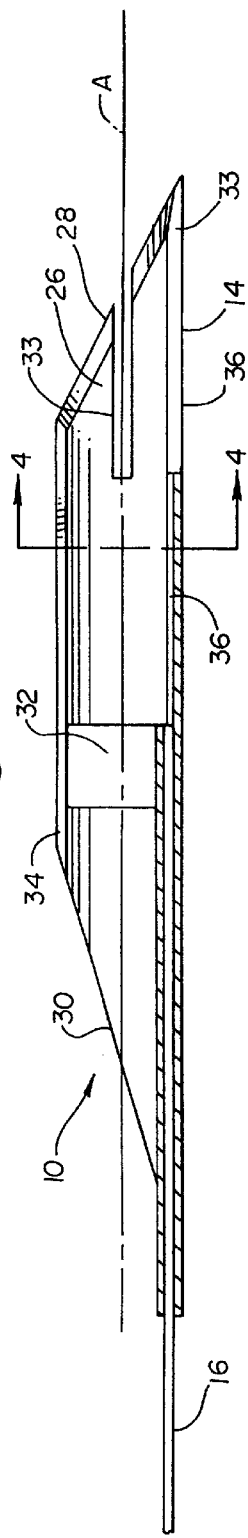
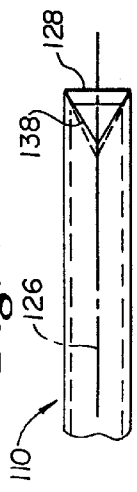
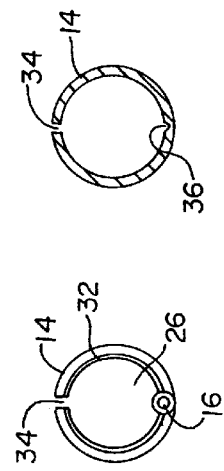
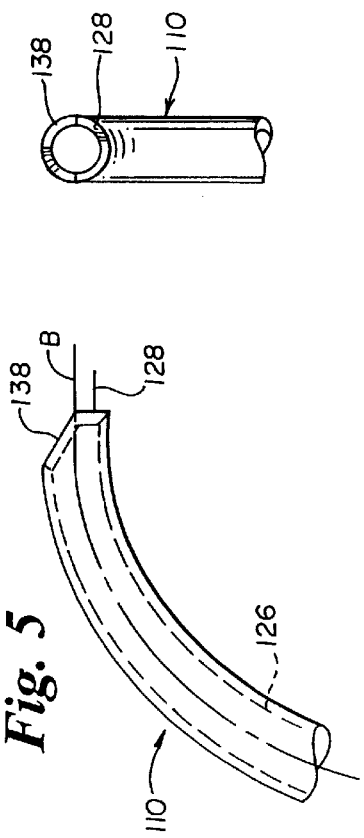

STENT SECURING CATHETER

BACKGROUND OF THE INVENTION

The present invention pertains generally to the field of stent securing catheters, and, in particular, to a stent securing catheter having a tapered distal end.

Stents are increasingly used in Percutaneous Transluminal Coronary Angioplasty (PTCA). PTCA is a well established procedure for dilating stenosed vessel regions in the heart. In this procedure, a balloon angioplasty catheter is introduced into the vasculature, typically through an incision in the femoral artery in the groin. The balloon catheter is advanced through the femoral artery, through the aortic arch, and into the artery to be treated. The balloon is advanced across a lesion and inflated, dilating the vessel at the location of the balloon expansion. The dilation increases the vessel cross sectional area and the resultant blood flow.

Over a period of time, the dilated vessel section may narrow again, in part due to a rebound from the angioplasty procedure, thereby reversing some of the benefits of the angioplasty. To prevent this vessel narrowing, stents are increasingly used. Stents are placed across the dilated region and radially expanded, opposing any inward radial force by the vessel walls.

Stents may be categorized as self-expanding and balloon expanding. The self-expanding stents are contained within a sheath to prevent premature expansion. The stent is placed within a guide catheter, moved across a lesion, withdrawn from the sheath, and the stent, being biased to expand, expands, ideally with sufficient force to resist the vessel wall rebound force which can occur after angioplasty. The stent can be left in place indefinitely.

Balloon-expandable stent deployment requires "tacking up" the stent, forcing stent struts or members radially outward into close proximity with the vessel wall. The stent is mounted over an uninflated balloon, crimped, and the balloon with stent advanced within a guide catheter. The balloon with stent is advanced distally out of the guide catheter across the lesion. The balloon is inflated, expanding the stent, thereby tacking the stent in place. For optimal stent placement, it is necessary for the stent to be properly positioned axially on the balloon prior to balloon inflation. A non-compliant balloon operated at high pressure is typically used to expand the inside diameter of the stent, forcing it against the vessel interior walls. The ballcon is deflated, and withdrawn proximally into the guide catheter.

For both types of stents, self-expanding and balloon expandable, a sheath can be used during stent delivery, being interposed between stent and guide catheter. The sheath adds a not-insubstantial thickness around the stent increasing the vessel inside diameter required to pass the sheathed stent. In one case, when using a sheath, a sheath outside diameter of 72 mils (thousands of an inch) is required to place a stent having an outside diameter of 60 mils. When not using a sheath, clearance is only required for the 60 mil sheath. This reduced outer diameter translates into increased vasculature accessible for stent placement, making treatable otherwise untreatable lesions.

As a result of the increased vasculature reachable without sheaths, treating physicians increasingly prefer to place stents without using a sheath, the "bare mounted" technique. This is possible with balloon-expanding stents, but has associated difficulties. A stent can be bare mounted over a balloon, crimped, and the balloon advanced through the guide catheter to the distal region of the guide catheter, which is positioned proximal to the vessel region having a lesion. The balloon with stent is advanced distally out of the guide catheter and across the lesion. When the stent is crimped onto the balloon, there can be a slight recoil, such that when balloon and stent are advanced out of the guide catheter, the stent is too large to be retracted into the guide catheter even before balloon inflation.

Occasionally, there are situations where the stent becomes partially or totally dislodged from the balloon. The dislodged stent may be detected while still within the guide catheter. A dislodged stent can be detected using radiography, observing relative positions of radiopaque regions on the stent and balloon catheter. When the stent is dislodged while within the guide catheter, it may be possible to withdraw the balloon catheter and stent together.

At other times, the stent becomes dislodged after the stent has been advanced out of the guide catheter. As the balloon-expanding stents do not self-expand, this creates the situation where a stent may become loose in the vasculature. When the stent is only partially dislodged from the balloon, the balloon with partially mounted stent may be withdrawn proximally into the guide catheter. The stent outer diameter is often only slightly less than the inner diameter of the guide catheter, to keep the guide catheter size down and increase the amount of vasculature open to the guide catheter. The stent outer diameter may be larger than the guide catheter inner diameter, and withdrawal of the balloon will not withdraw the stent, but may instead force the stent off the balloon.

In cases where the stent remains sufficiently small to fit within the guide catheter, withdrawal may still prove problematic. During attempted recovery, there is a point at which the proximal edge of the stent is to be withdrawn proximally past the distal edge of the guide catheter. If the stent is not centered relative to the longitudinal axis of the guide catheter, the guide catheter distal edge may catch against the stent proximal edge, forcing the stent from the balloon.

SUMMARY OF THE INVENTION

The present invention pertains generally to a stent securing catheter for aiding in the withdrawal of a stent disposed on a stent delivery catheter from a coronary artery. The catheter of the present invention aids in guiding the proximal end of a stent into a guide catheter while reducing the potential that the stent will be dislodged from the delivery catheter.

The stent securing catheter in accordance with the present invention includes a tubular body having a longitudinal axis. The tubular body defines a stent receiving lumen, the tubular body has a proximal end and a distal end. The distal end defines an opening into the receiving lumen. The opening is disposed at a generally acute angle to the longitudinal axis. The opening into the receiving lumen is preferably beveled to guide a stent into the stent receiving lumen.

In one embodiment, the tubular body can be disposed at the distal end of an elongate shaft or wire. Preferably the proximal end of the tubular body is disposed at a generally acute angle to the longitudinal axis of the tubular body. By disposing the proximal end of the tubular body at an acute angle, the tubular body may more readily be drawn through the distal end of a guide catheter if it were to be advanced beyond the distal end of the guide catheter into a body lumen.

To place the tubular body around or on a guide wire or delivery catheter, the tubular body preferably includes a slot extending from outside the body into the stent receiving lumen. The slot preferably extends between the proximal and distal ends of the tubular body. The tubular body can include a hinge disposed generally parallel to the slot to aid in expansion of the slot for receipt of the guide wire or delivery catheter therethrough.

In an alternate embodiment of the stent securing catheter in accordance with the present invention, the catheter may be formed and used in the manner of a conventional guide catheter, except that the opening disposed at the distal end of the catheter is preferably disposed at an acute angle to the catheter's longitudinal axis. The catheter can advantageously include a curve proximate its distal end to aid in the positioning of the catheter into the ostium of a coronary artery.

BRIEF DESCRIPTION OF THE DRAWINGS

FIG. 1 is a side view of an embodiment of the stent securing catheter disposed within a guide catheter and having a stent and stent delivery balloon disposed therein;

FIG. 2 is a side view of the stent securing catheter of FIG. 1;

FIG. 3 is a proximal end view of a tubular body of the stent securing catheter of FIG. 2;

FIG. 4 is a cross-sectional view of the catheter of FIG. 2;

FIG. 5 is a side view of the distal end of an alternate embodiment of a stent securing catheter in accordance with the present invention;

FIG. 6 is a top view of the catheter of FIG. 5; and

FIG. 7 is an end view of the catheter of FIG. 5.

DETAILED DESCRIPTION OF THE INVENTION

Referring now to the drawings wherein like reference numerals refer to like elements throughout the several views, FIG. 1 is a side, cross-sectional view of a stent securing catheter 10 in accordance with the present invention. Stent securing catheter 10 is shown disposed within a typical guide catheter 12. Catheter 10 includes a tubular body 14 disposed at the distal end of an elongate shaft 16. A typical balloon expandable stent 18 is shown disposed on a balloon expandable stent delivery catheter 20 having a balloon expandable portion 22. As usual, balloon expandable portion 22 is disposed at the distal end of delivery catheter 20. The proximal end 24 of stent 18 is shown within a stent receiving lumen 26 defined by tubular body 14.

In a typical situation, stent 18 will be delivered across a dilated coronary lesion on balloon expandable portion 22 by way of guide catheter 12. When stent 18 is delivered to the coronary lesion, it will be disposed distally of the distal end of guide catheter 12. Should it be necessary, however, to withdraw stent 18 on delivery catheter 20, it can be appreciated that the proximal end 24 of stent 18 may encounter the distal end of guide catheter 12. If proximal end 24 of stent 18 should collide with the distal end of guide catheter 12, stent 18 may be dislodged from delivery catheter 20. If, however, distal end 24 of stent 18 is disposed within stent receiving lumen 26 of stent securing catheter 10 prior to withdrawal through catheter 12, such a collision and resultant stent dislodgement will not occur.

FIG. 2 is a side view of a stent securing catheter 10. Tubular body 14 of catheter 10 includes a distal end 28 and a proximal end 30. A longitudinal axis of tubular body 14 is shown by line A. Distal end 28 is disposed at an acute angle to longitudinal axis A and defines an opening into stent receiving lumen 26. Distal end 28 is preferably beveled around its circumference to create a funneling profile at distal end 28 into stent receiving lumen 26. Proximal end 30 is also preferably disposed at an acute angle to longitudinal axis A. Proximal end 30 defines an opening at an acute angle into stent receiving lumen 26.

Elongate shaft 16 is shown extending into a tight lumen formed within tubular body 14. The distal end of elongate shaft 16 can be secured within the tight lumen by adhesive or friction fit. Elongate shaft 16 is preferably long enough and flexible enough to reach from a coronary lesion through the aorta into and out of a femoral artery access point or other access route as known in the art of coronary angioplasty or stenting procedures. An optional radiopaque marker band 32 is shown disposed within stent receiving lumen 26 and soldered or adhered to the distal end of shaft 16.

Also shown in FIG. 2 is an additional optional feature which may be incorporated into the stent securing catheter 10 of the present invention. This feature is a series of slits 33 made into the distal end of tubular body 14. These slits can be disposed at intervals around tubular body 14, for example, at 90° intervals. Slits 33 will allow that portion of tubular body 14 disposed between slits 33 to deflect outwardly as a stent is guided proximally into stent receiving lumen 26. This, of course, assumes that the material which is used to form tubular body 14 is sufficiently flexible to allow these areas to flex when the stent or catheter collides with them.

FIG. 3 is a proximal end view of stent securing catheter 10 as shown in FIG. 2. In this view, radiopaque band 32 can be seen disposed within lumen 26. A longitudinally extending slot 34 is shown defined through tubular body 14.

FIG. 4 is a cross-sectional view of tubular body 14 of stent securing catheter 10 taken transversely through catheter 10 of FIG. 2. A longitudinally extending indentation or hinge 36 in tubular body 14 is shown opposite slot 34.

Tubular body 14 is preferably formed from a polymer such as PEBAX. Elongate shaft 16 can preferably be formed from a stainless steel wire and marker band 32 from a substantially radiopaque material such as platinum or gold. It can be understood that numerous other materials of construction could be used to form the various components of catheter 10. Those skilled in the art of catheter construction will be aware of various bio-compatible materials which can advantageously be used to form and assemble the various elements of catheter 10.

In use, when it is desirable to withdraw a stent 18 disposed on a delivery catheter 20 from a lesion, slot 34 is spread apart such that a proximal end of delivery catheter 20 can be longitudinally disposed within stent receiving lumen 26. Hinge 36 can provide a weak region within tubular body 14 such that slot 34 can more readily be expanded to accommodate the diameter of delivery catheter 20. Once the proximal portion of delivery catheter 20 is disposed within stent receiving lumen 26, stent securing catheter 10 can be advanced over delivery catheter 22 proximal end 24 of stent 18. Catheter 10 can then be further advanced such that at least proximal end 24 of stent 18 is received through the opening at distal end 28 of tubular body 14 into stent receiving lumen 26.

It can be appreciated that since the distal opening into stent receiving lumen 26 is disposed at an acute angle and that the circumference of distal end 28 of tubular body 14 is beveled inward toward lumen 26, proximal end 24 of stent 18 will be readily received through the distal opening into stent receiving lumen 26. Once proximal end of stent 18 is within stent securing catheter 10, stent 18 can be withdrawn into guide catheter 12 without concern that proximal end 24 of stent 18 will collide with the distal end of guide catheter 12.

FIG. 5 is a side view of an alternate embodiment of a stent securing catheter 110. Stent securing catheter 110 can be formed from a standard guide catheter as described in more detail below. In such a way, stent securing catheter 110 can be used as a conventional guide catheter, but includes an advantageous feature which can more readily guide a proximal end of a stent into the stent receiving or guide catheter lumen 126.

As shown in FIG. 5, stent receiving catheter 110 extends along a longitudinal axis shown by the line B to a distal end 128. Distal end 128 defines a distal opening into stent receiving lumen 126. Distal end 128 is preferably disposed at generally an acute angle to the longitudinal axis. This can be accomplished by forming a V-shaped notch 138 in one side of catheter 110. The periphery of distal end 128 including notch 138 is preferably beveled inward toward lumen 126.

FIG. 6 is a top view of catheter 10 of FIG. 5 showing V-shaped notch 138 at distal end 128. FIG. 7 is a distal end view of catheter 110. This figure offers a direct view into the opening at distal end 128.

Catheter 110 is preferably formed in all respects as a conventional guide catheter except in the configuration of distal end 128 as described above and by reference to the figures. This will allow catheter 110 to act both as a standard guide catheter and a stent securing catheter during the same procedure.

In use, stent securing catheter 110 is used as a typical guide catheter. After stent 18 disposed on a balloon catheter 20 has been advanced across a lesion distally of distal end 128, the acute angle of the opening at distal end 128 and the beveling of the distal end will present an advantageous profile for withdrawal of the stent into the delivery catheter if desired. The profile of end 128 will more readily guide distal end 18 of stent 14 into lumen 126 than a standard guide catheter distal end disposed neither at an acute angle nor having a beveled opening.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A stent securing catheter, comprising:

a tubular body, having a longitudinal axis, and defining a stent receiving lumen, the tubular body having a proximal end and a distal end, wherein the distal end defines an opening into the receiving lumen, the opening being disposed at a generally acute angle to the longitudinal axis;

wherein the opening into the receiving lumen is beveled to guide a stent into the stent receiving lumen;

wherein the proximal end of the tubular body is disposed at a generally acute angle to the longitudinal axis of the tubular body;

wherein a slot extends from outside the tubular body into the stent receiving lumen between the proximal and distal ends of the tubular body;

wherein the tubular body includes a hinge disposed generally parallel to the slot; and an elongated shaft having a proximal end and a distal end, the tubular body being disposed at the distal end of the shaft.

2. A stent securing catheter in accordance with claim 1, wherein the tubular body curves along its longitudinal axis proximate its distal end.

3. A method of aborting a stent deployment, comprising the steps of:

providing a stent securing catheter having a tubular body having a longitudinal axis and stent receiving lumen, the tubular body having a proximal end and a distal end, wherein the distal end defines an opening into the receiving lumen, the opening being disposed at a generally acute angle to the longitudinal axis; and advancing the stent securing catheter over the proximal end of a stent disposed on a stent delivery catheter within a body lumen such that the proximal end of the stent is received within the stent receiving lumen through the opening.

4. The method in accordance with claim 3, further comprising the step of withdrawing the stent and securing catheter into a guide catheter.

5. The method in accordance with claim 3, further comprising the step of withdrawing the stent through the stent securing catheter.

6. A stent securing catheter, comprising:

a tubular body, having a longitudinal axis, a stent receiving lumen, a proximal end and a distal end;

wherein the distal end of the tubular body defines an opening into the receiving lumen, the opening being disposed at a generally acute angle to the longitudinal axis;

wherein the proximal end of the tubular body defines an opening into the receiving lumen, the opening being disposed at a generally acute angle to the longitudinal axis;

an elongated shaft having a proximal end and a distal end;

wherein the tubular body is disposed at the distal end of the shaft;

the tubular body including a slot extending from outside the tubular body into the stent receiving lumen between the proximal and distal ends of the tubular body;

the tubular body including a plurality of slits disposed proximate the distal end of the tubular body;

the slits extending from the outside of the tubular body into the stent receiving lumen; and the length of the slits being less than the length of the tubular body.

* * * * *